United States Patent [19]

Stetter et al.

[11] 4,326,927
[45] Apr. 27, 1982

[54] METHOD AND DEVICE FOR THE DETECTION AND MEASUREMENT OF ELECTROCHEMICALLY ACTIVE COMPOUNDS

[75] Inventors: Joseph R. Stetter, Naperville, Ill.; Donald R. Rutt, Merrick, N.Y.

[73] Assignee: Becton, Dickinson and Company, Paramus, N.J.

[21] Appl. No.: 172,170

[22] Filed: Jul. 25, 1980

[51] Int. Cl.$^3$ .................. G01N 27/46; G01N 27/52
[52] U.S. Cl. ............................... 204/1 T; 204/195 R; 204/195 P
[58] Field of Search ............... 204/195 P, 195 R, 1 N, 204/1 K, 1 F

[56] References Cited

U.S. PATENT DOCUMENTS

| | | | |
|---|---|---|---|
| 3,689,394 | 9/1972 | Davies et al. | 204/195 P |
| 4,001,103 | 1/1977 | Blurton et al. | 204/195 R |
| 4,182,666 | 1/1980 | Dickinson et al. | 204/195 P |
| 4,201,634 | 5/1980 | Stetter | 204/1 T |

FOREIGN PATENT DOCUMENTS 1200595  7/1970  United Kingdom ........... 204/195 P

Primary Examiner—G. L. Kaplan

[57] ABSTRACT

An electrochemical sensing device comprising a sensing electrode, a counter electrode, an electrolyte in contact with said sensing electrode and counter electrode, said sensing electrode comprising a porous hydrophobic substrate having vapor-deposited thereon a porous film of a catalyst to provicde a diffusion electrode, means for exposing said sensing electrode to the gas to be detected, means electrically coupled to said sensing electrode for maintaining said sensing electrode at a potential of about 0.4 volt to about 1.5 volt with respect to the potential of the reversible hydrogen couple in the electrolyte of said cell, and means for measuring current flowing between said sensing electrode and said counter electrode which measured current is a measure of the concentration of the noxious gas being detected.

5 Claims, 3 Drawing Figures

# METHOD AND DEVICE FOR THE DETECTION AND MEASUREMENT OF ELECTROCHEMICALLY ACTIVE COMPOUNDS

BACKGROUND OF THE INVENTION

1. Field of Invention

The present invention relates to a device and method for the detection and measurement of electrochemically active compounds, especially pollutants, such as $SO_2$, $H_2S$, $NO_x$, and hydrazines. More particularly, the device is for detection of these pollutants in the presence of high concentrations of other pollutants and at lower levels than previously capable of detection.

2. Discussion of Prior Art

In recent times a greater awareness has developed regarding the danger of human exposure to a wide variety of chemicals found in urban, suburban, and industrialized areas. Not only are high doses of toxic compounds hazardous (perhaps lethal) but adverse health effects are found to be caused by low level exposure over a long time period. Such toxic compounds are used in industry and in the home, and it is recognized that pollutant emission sources exist virtually everywhere.

Because of the ubiquitous nature of pollution and the deleterious health effects it can produce, there arises a need to both monitor and control pollutant emissions and human exposure to same. This invention is directed toward measurement of toxic gases and some of these electrochemically active compounds which are carcinogenic in nature.

Sensitive instrumentation is necessary to measure low levels of $SO_2$, $H_2S$, NO, $NO_2$, hydrazines, and the like so that the safety and health of the worker and the population in general, can be properly protected. A problem encountered in the development of such equipment is the difficulty experienced in the detection of low concentrations of the toxic gas being sensed or monitored, in the presence of high concentrations of CO and other interfering gases which are frequently present. A further problem is encountered when the instrument zero drift and noise is large and the signal being measured is small, thus limiting the useful lower detectable limit of such devices. Hence, although the electrochemical activity is known for a variety of pollutants, development of highly sensitive and highly selective instrumentation has been hindered.

One approach taken to improve the selectivity of the electrochemical sensors for these gases in the presence of CO has been to use a gold catalyst for the sensing electrode as described, for instance, in U.S. Pat. No. 3,776,832 to Oswin et al. This approach, however, has only been partially successful. For example, typical discrimination ratios for $NO_2$ and $H_2S$ in the presence of CO are $-1000/1$ and $2000/1$, respectively. (The negative signal for the $NO_2$/CO ratio indicates that $NO_2$ is electro-reduced whereas CO is electro-oxidized under the preferred conditions for device operation). Therefore, 1000 ppm CO will give a signal equivalent to minus 1 ppm $NO_2$ (negative deflection on instrument meter), and 2000 ppm CO will give a signal equivalent to 1 ppm $H_2S$. Ten ppm CO will give a reading equivalent to 10 ppb $NO_2$ (a 50% error in $NO_2$ signal of a typical ambient) and a reading equivalent to 5 ppb $H_2S$ (a 100% error in $H_2S$ signal in a typical ambient). The magnitude of these percentage errors clearly points out the shortcomings of electrochemical instrumentation employing gold working electrodes in the detection of these pollutant gases in the presence of CO at usual ambient levels.

Similarly, the use of the carbon-supported gold catalyst as described in U.S. Pat. No. 4,042,464 (Blurton & Sedlak) has reduced the CO signals such that discrimination ratios are $-10,000/1$ and $20,000/1$ for $NO_2$ and $H_2S$, respectively. This is an improvement but yet accuracy is limited at the lower levels.

In addition, both of these prior art systems also possess a limitation as to their ultimate usefulness since when measuring very low concentrations of noxious gases the background current tends to drift. Background fluctuations are typically in the range of $\pm 10$ ppb over the course of several hours making continuous zero adjustment necessary for accurate measurements as well as causing appreciable instrument instability when measuring low levels continuously.

OBJECTS AND GENERAL DESCRIPTION OF THE INVENTION

Accordingly, a primary object of the present invention is to provide a compact, inexpensive, and easy-to-operate sensing device for accurately and reproducibly detecting and quantitatively determining low concentrations of noxious gases in the presence of high concentrations of CO and other atmospheric gases.

Another object of this invention is to provide a method for electrochemically detecting low concentrations of noxious gases in a gaseous medium.

Another object of this invention is to provide very effective gas sensors of improved stability.

Another object of this invention is to provide a sensor characterized by specific electrocatalytic properties and an enhanced sensitivity for gas sensing.

SUMMARY OF THE INVENTION

The aforementioned objects of the present invention are obtained by an electrochemical sensing device comprising a sensing electrode, a counter electrode, an electrolyte in contact with said sensing electrode and counter electrode, said sensing electrode comprising a porous hydrophobic substrate having vapor-deposited thereon a porous film of a metal catalyst, preferably a noble metal catalyst, to provide a diffusion electrode, means for exposing said sensing electrode to the gas to be detected, means electrically coupled to said sensing electrode for maintaining said sensing electrode at a potential of about 0.4 volt to about 1.5 volt with respect to the potential of the reversible hydrogen couple in the electrolyte of said cell, and means for measuring current flowing between said sensing electrode and said counter electrode which measured current is a measure of the concentration of the noxious gas being detected.

It has been surprisingly found that the vapor-deposited metal catalyst diffusion electrode of the invention results in a sensing electrode having enhanced stability characterized by lower background currents and less drift therein, higher sensitivity, and an enhanced selectivity over prior art noxious gas sensing electrodes.

Furthermore, another advantage offered by the sensing electrode of the invention is that it can be treated by physical and chemical methods to significantly enhance and change the nature of its selective electro-catalytic activity. By way of illustration, when a sensing electrode according to the invention comprising untreated vapor-deposited Au is used in the detection and monitoring of $H_2S$, typical discrimination ratios for $H_2S$ in the presence of CO are 100,000/1 which is 10 times more selective than prior art systems. This means that one can monitor $H_2S$ in the presence of CO at levels 10 times lower than the prior art system with the same level of interference. However, when the vapor-deposited Au sensing electrode is subjected to treatment with a reducing gas at elevated temperatures, e.g. treatment with $H_2$ at 200° C. for 2-8 hours, there results a loss in sensitivity for $NO_2$ in certain potential regions. This means that selectivity for $H_2S$ in the presence of $NO_2$ is achieved, and typical discrimination ratios become 500/1 instead of 2/1, a several hundred-fold increase over prior art sensing systems. As a result, $H_2S$ can now be analyzed in the presence of $NO_2$, and this was not possible with prior art systems. Similarly, the preparative technique of curing in $H_2$ or $O_2$ or mixtures thereof can be used to tailor the electrocatalytic properties of the vapor-deposited noble metal film deposited electrode for other gas detection modes. By way of example, a Au surface can be treated such that $NO_2$ signals are enhanced instead of destroyed (as above). Similarly, signals can be enhanced or destroyed for $SO_2$ or NO. Other methods, chemical or electrochemical in nature, might be suitable to enhance or reduce the relative sensitivity of the vapor-deposited metal films.

The unexpected nature of the invention is underscored by the fact that the catalytic activity of a porous vapor-deposited metal electrode upon a porous support is significantly different from all prior metal electrode systems in the art of gas detection. One would anticipate that the catalytic activity of vapor-deposited metal electrodes would be significantly lower than prior art metal electrodes, since prior art metal electrodes use high-surface-area powders and dispersion techniques to prepare high-surface-area metal catalysts. Higher-surface-area materials generally result in higher catalytic activity and higher sensitivity. It was surprising to find that the electrode of the invention retains the high catalytic activity that characterizes a high-surface-area catalyst for the noxious gas being detected, but has significantly lower catalytic activity for other, normally electrochemically active, noxious gases. This finding was in conflict with the expected overall decrease in catalytic activity.

The sensing electrode can take any suitable form. For instance, any suitably porous yet hydrophobic solid substrate such as a membrane or sheet can be used upon which the catalyst layer can be vapor-deposited. Suitable porosity is defined herein and in the appended claims to mean porous enough to allow the noxious gas molecules being sensed to reach the deposited metal electrocatalyst. The substrate should be sufficiently hydrophobic to retain the electrolyte liquid so that the internal electrolyte of the cell remains captive. The catalyst (e.g., Ni, Au, Ag, Pt, Pd, Ir, Os, Rh, Ru) onto one side of the substrate can be applied by any suitable vapor deposited technique which produces an ultra-high-purity film of the electro-catalyst (e.g., 99.9% purity). Illustrative of suitable techniques are vacuum vapor deposition or sputtering. The hydrophobic substrate containing the layer of vapor-deposited or sputtered catalyst, must remain porous. The metal coatings therefore must not be so thick as to substantially eliminate porosity but not so thin that catalytic activity and electrical conduction are high. Metal films between 200 Å and 20,000 Å have been used successfully, the optimum film thickness depending upon the particular metal, the porosity of the substrate, the conductivity of the deposit and the noxious gas to be detected. The substrate can have a wide variety of pore sizes, but typically 0.1-0.5 micron form a very good electrode.

A preferred method for an $H_2S$ electrode involves vapor deposition of a moderately thick film of between 2,000 Å and 10,000 Å upon a porous Teflon membrane with 0.1 to 1 micron pore size, followed by a heat treatment in $H_2$ at 200°-300° C. for approximately 2-8 hours.

A preferred method for an $SO_2$ or $NO_2$ sensing electrode involves vapor deposition of a relatively thick noble metal film of 5,000-20,000 Å upon a porous Teflon substrate followed by heating in air at 200° C. for 2-5 hours.

It is apparent that the catalytic activity is due to the specific nature of the surface. Obviously, heating in a reducing atmosphere such as $H_2$ causes a reduction of existing oxides, while heating in an oxidizing atmosphere such as air causes a thermally oxidized surface to be created. Similarly, an electrochemically active oxide can be generated when the catalyst is placed in an electrochemical cell and potentiostated at a significantly anodic bias (several electrochemical oxides are possible and, depending upon the potential used, a certain oxide will be formed preferentially). Each of these treatments will provide for an improved detection surface for one specific member of the noxious gases.

The sensor of the invention can be either a two-electrode system or a three-electrode system. Of the two systems, the three-electrode system is preferred for certain noxious gas detection systems and includes a reference electrode in addition to the sensing electrode and counterelectrode. The reference electrode of the electrochemical cell must be capable of maintaining a relatively constant potential in the environment of the electrochemical cell. Preferred reference electrodes are catalyzed air electrodes of the diffusion type such as Pt-catalyzed air electrodes and Ir-catalyzed air diffusion electrodes. The third or reference electrode can be positioned between the sensing electrode and counterelectrode, or it can be positioned on the same plane or on the same substrate as the sensing electrode and/or counterelectrode. It is only necessary that the electrodes of the electrochemical cell be in contact only via the electrolyte. Thus, a polymer substrate such as porous polytetrafluoroethylene can have two or three separate and distinct portions coated with a catalytic material such as platinum, or an admixture of platinum and PTFE particles. The entire substrate will, therefore, function as both the counterelectrode and reference electrode. As will be more fully apparent hereinafter, various designs of layouts can be used.

Reference electrode, as the term is used herein, defines an electrode at which no, or substantially no, current flows. Accordingly, the reference electrode and sensing electrode must be connected through electronic circuitry, or the like, to preclude or minimize current flow between the reference electrode and sensing electrode, so as to define and maintain a known reference potential. Although it is virtually impossible to completely eliminate current flow, the reference potential cannot show extensive drift, i.e., more than about ±25 mV; or rapid drift, i.e., more than ±5 mV, over a period of 10 seconds. If extensive or rapid drift occurs, a false reading as to the quantity of the detected gas may be obtained. As is apparent, the actual extent of potential drift depends upon the accuracy of the measurement needed. If high accuracy is necessary, a greater current potential drift cannot be tolerated over any length of time.

The specific structure of the counterelectrode employed in the electrochemical cell is not critical. Where the sensing electrode of the sensor catalyzes electrooxidation of the gas to be detected it is only essential that the counterelectrode be comprised of a material at which electrochemical reduction occurs. On the other hand, where the sensing electrode catalyzes electroreduction of the gas to be detected, it is only essential that the counterelectrode be comprised of a material at which electrooxidation occurs. In most instances, the selection of the particular counterelectrode will depend upon whether a 2-electrode or 3-electrode system is employed. When a 3-electrode system is utilized, the cathodic and anodic counterelectrodes are usually noble metal electrodes such as platinum or gold electrodes. When a 2-electrode system is utilized, the preferred cathodic counterelectrode is lead dioxide or maganese dioxide and the preferred anodic counterelectrode is a hydrogen electrode.

One of the problems which may be encountered in the utilization of measuring equipment, such as the cell of the present invention, relates to the fact that an oxygen-water redox couple will be potentially available within the electrochemical cell to generate undesired current in the external circuit which current is not derived from reaction of the noxious gas to be detected. Such a redox couple results from oxygen contained in the incoming atmospheric air and water contained in the electrolyte. For example, under certain circumstances water may become oxidized at the sensing electrodes of the cell, thereby generating current in the external circuit that would not be distinquishable from the current generated by the noxious gas reaction. Likewise, oxygen may undergo reaction at the sensing electrode thereby similarly generating undesired current. For this reason, means are provided with the electrochemical cell of the invention for maintaining the sensing electrode at a potential of about 0.4 V to 1.5 V with respect to the potential of the reversible hydrogen couple in the electrolyte of the cell. It has been found that a fixed potential within this range creates a condition whereby the oxygen-water couple produces in the external circuit no discernible current relative to the current produced by the reaction of the noxious gas to be detected.

The potential selected within this range will depend upon the electrode treatment, the particular noxious gas being detected, and the electrolyte ($H_2SO_4$, KOH or non-aqueous). In the case of $H_2S$, it can be measured throughout the potential range, using a reduced thin Au electrode film in KOH or $H_2SO_4$. For maximum accuracy during $SO_2$ measurement, it should be detected on an oxidized or air-treated thick, film of Au in the potential region. Likewise $NO_2$ should be detected on a high-loading Au surface which has been oxidized but only at potentials less than 1.0 V in KOH or $H_2SO_4$ electrolyte, while for NO one should use a thin film oxide formed at between 1.0 and 1.5 volts in $H_2SO_4$.

The means for maintaining the potential within the prescribed range can be any suitable means. In the case of a 3-electrode system, it can be a potentiostat and, in the case of a 2-electrode system, it can be a potential-divider. One can use a potentiostat with a common counter and reference electrode but this allows the reference voltage to float with the potential of the counterelectrode. Then the counterelectrode must be non-polarizable or the value of the potentiostat in maintaining a constant potential for the working electrode is lost.

The electrolyte employed in the electrochemical cell of the present invention can be either an aqueous acid or an aqueous alkaline solution. The electrolytes can be free flowing or trapped in a suitable matrix. In the event a matrix is employed, the matrix material must be sufficiently hydrophilic to permit continuous wetting of the sensing electrode and the counterelectrode surface as well as the surface of the third or reference electrode when a three-electrode system is employed. Materials such as asbestos, Kraft paper, polyvinylalcohol, polyvinylchloride which has been treated to render it hydrophilic, or the like can be selected.

The means for measuring the current flowing from the sensing electrode to the counterelectrode can be any suitable readout means such as an ammeter or a high performance digital readout device. The reading taken will be representative of the electrochemical reaction occurring at the sensing electrode and of the quantity of material reacted. The ammeter or readout device may be readily calibrated in a known manner to provide determination of the quantity of noxious gas occurring in the air sample taken.

In operation, the detecting unit of the invention will include sample intake means and means to draw the flow of the gas sample through the cell, preferably at a controlled flow rate. The control of the flow rate of the sample can be accomplished in various ways. In most instances, however, the means for drawing the gas through the intake means into the cell will effectively pass a predetermined quantity of gas per unit time to a predetermined surface area of the sensing electrode, thus assuring continuous accuracy in the quantitative measurement. Preferably, the quantity of gas fed to the sensing surface is controlled by a constant flow control means of the conventional type which feeds the gas sample to the electrochemical cell at a constant rate.

Pumping or suction can be employed to draw the gas sample to the detecting electrode of the cell but simple gaseous diffusion may also be utilized. In the case of diffusion, the sensing electrode is merely exposed to the noxious gas by positioning it in the atmosphere which is being sensed. Many specific geometric designs are possible and have been previously described as for instance in U.S. Pat. No. 3,776,832.

The sensing element of the present device can be used to detect specifically $H_2S$, $SO_2$, $NO_2$, NO, and hydrazines but there are cases where overlap of signals (or interference) may still sometimes occur. Thus, when it is desired to detect noxious gases and an overlap in signal still occurs, it may be necessary to employ a selective scrubber between the sampled gas stream and the sensing electrode. For instance, in the detection of NO both $NO_2$ and $H_2S$ can be excluded by using an adsorbent of triethanolamine and lead acetate upon a suitable support which contact the gas before analysis.

In many cases the noxious gas to be detected will be present at high concentrations compared to the interferent and direct detection is possible.

The housing of the electrochemical cell can be made of any suitable material which does not form soluble oxidizable products. Plastics such as the olefinic polymers are preferred and the housing is advantageously designed to permit the sensing electrode to have an area exposed to ambient air.

BRIEF DESCRIPTION OF THE DRAWINGS

The detecting device of the present invention will be more readily apparent from the accompanying drawing wherein like numerals are employed to designate like parts.

In the drawing.

DETAILED DESCRIPTION OF PREFERRED EMBODIMENT

Figure 1:
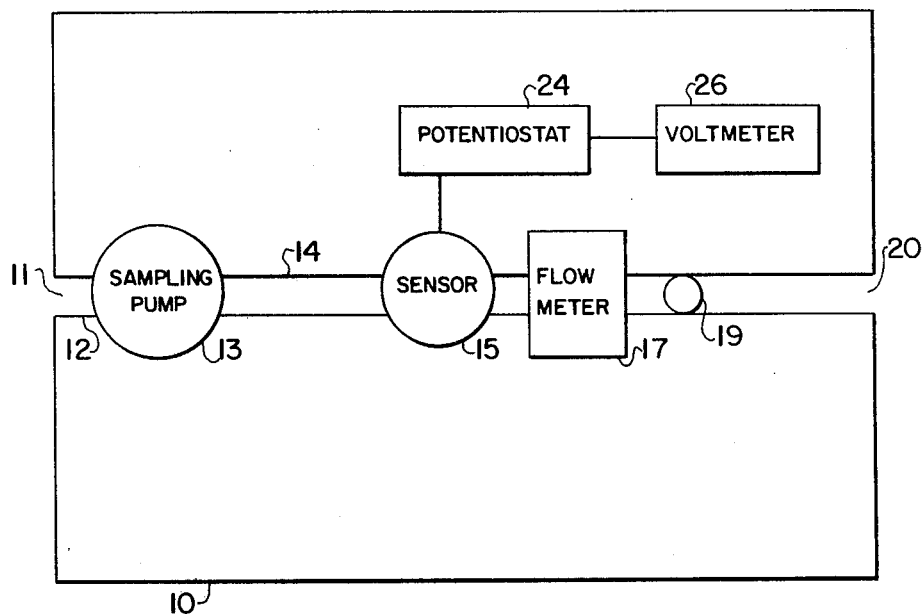
FIG. 1 is a diagrammatic view in block form of a preferred embodiment of the present invention.

More specifically, referring to FIG. 1, the detecting device for the measurement of a noxious gas such as $H_2S$, $SO_2$, $NO_x$ or a hydrazine (e.g. monomethyl-hydrazine or unnsymmetrical dimethyl-hydrazine), is positioned within a housing 10. The device includes a sample intake means 11 in direct communication via line 12 with a sampling pump 13. The pump 13 communicates with the sensor (i.e. electrochemical cell) 15 via line 14 which in turn communicates with flow meter 17. Gas flowing through the sensor 15 exits via exhaust outlet 20. A flow control means such as a valve 19 is positioned between the flow meter and exhaust 20. The sensor is provided with a potentiostat 24 for maintenance of the fixed relative potential between the anode and the reference electrode of sensor 15 and a voltmeter 26. The potentiostat is hooked up to an electronic circuit described below which includes an amplifier and voltmeter. Noxious gas intake 11, line 12, sample pump 13, line 14 and the housing of sensor 15 are all constructed of FEP Teflon.

Figure 2:
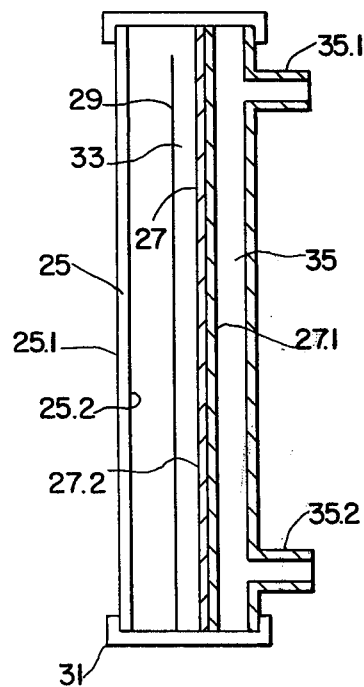
FIG. 2 is a cross-sectional view of the electrochemical cell of the detector unit.

Electrochemical sensor 15 as seen most clearly from FIG. 2, will include a cathode 25, an anode 27 (sensing electrode) and a third or reference electrode 29, all positioned within a housing 31. In the embodiment of FIG. 2, the cathode, anode, and third electrode are in contact with a free-flowing aqueous KOH electrolyte 33. Adjacent anode 27 is reactant chamber 35 having reactant gas inlet 35.1 which is in direct communication with intake 11 and outlet 35.2. In the embodiment shown, cathode 25 is in direct communication with atmospheric air. Both the anode and cathode are lightweight electrodes comprising a hydrophobic plastic substrate 27.1 and 25.1 in direct contact with reactant chamber 35 in the case of the anode, and with the ambient environment in the case of the cathode. Catalytic film layers 27.2 and 25.2 respectively, have been vapor deposited on hydrophobic plastic substrates 27.1 and 25.1 by vacuum vapor deposition to a film thickness of 1000 Å to 20,000 Å and are in contact with the electrolyte of the cell. The catalytic layer 27.2 of the sensing electrode 27 may be a layer of Au, Rh, or any other appropriate metal vacuum-vapor-deposited onto hydrophobic substrate 27.1 as a layer at a loading of preferably 5–50 mg/cm$^2$, more preferably 5–30 mg/cm$^2$. Catalytic layer 25.2 of the cathode 25 may comprise a film of platinum (or any other appropriate metal) vapor-deposited or sputtered. Reference electrode 29 may be a porous, platinum catalyzed PTFE diffusion electrode which comprises film of platinum approximately 7 mils thick vapor-deposited or sputtered on a polytetrafluoroethylene substrate. A fixed potential of about 0.4 volt to 1.5 volts depending upon the gas to be detected, with respect to a reversible hydrogen electrode in the same electrolyte is maintained on the anode by means of the reference electrode through the potentiostat 24. The anode, cathode and reference electrode of the cell are connected through the electrical circuit, shown in FIG. 3. The applied potential at the working electrode (anode) relative to the counterelectrode (cathode) is positive in this case.

Figure 3:
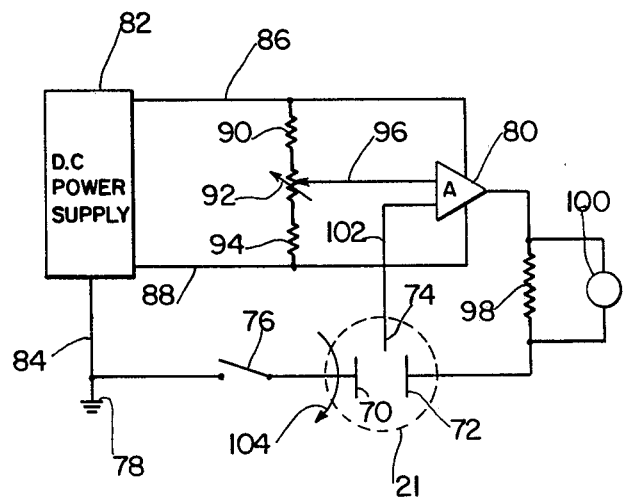
FIG. 3 is a schematic diagram of a potentiostat circuit for controlling operation of the cell and particularly as applied in maintaining a fixed potential between the working electrode and a reference electrode.

The circuitry for the maintenance of a fixed relative potential between the working electrode and reference electrode is shown in FIG. 3. FIG. 3 depicts a potentiostat circuit which is generally arranged in accordance with conventional principles within the knowledge of those skilled in the art and which enables the maintenance of the fixed relative potential between the working electrode and the reference electrode without development of current flow therebetween. The circuit also operates to enable appropriate current flow in the external circuit between the working electrode and the counterelectrode when the gas to be detected is reacted within the electrochemical cell.

In FIG. 3, the electrochemical cell 21 is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92 and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected thereacross. The reference electrode 74 is connected to the operational amplifier 80 through a lead 102, and as the relative potential between the reference electrode 74 and the anode 70 develops a tendency to vary from the fixed level established by adjustment of the rheostat 92, the amplifier 80 operates through a negative feedback to maintain constant the relative potential between the anode 70 and the reference electrode 74. The factor creating the tendency to alter the anode reference electrode fixed relative potential is developed as a result of reaction at the anode 70 of the impurity to be detected, i.e. oxidation of the noxious gas to be detected contained within the gas sample flowing across the face of the anode 70 as indicated by the arrow 104. The output current of the operational amplifier 80 will pass through the resistor 98 and will be a result of and related to the level of oxidation occurring at the anode 70. Therefore, the reading taken at the voltmeter 100 will be representative of the oxidation reaction occurring at the anode 70 and the quantity of material oxidized.

In operation, therefore, assuming the desirability of measuring the concentration of a given noxious gas in the atmosphere, the atmospheric air containing the noxious gas is introduced into inlet 11 and pumped by pump 13 through line 14 at a metered rate into the sensor. In sensor 15 the air sample passes over the anode therein setting off electrooxidation of the noxious gas impurity contained therein. This electrochemical reaction produces a current in the external circuit of the cell thereby enabling detection and measurement of the impurity concentration as by use of a voltmeter.

The following Example I is included as illustrative of a suitable method for the preparation by vapor deposition of a gold diffusion electrode of the present invention.

EXAMPLE I

A tungsten (W) wire basket resistance-heated vapor source is first outgassed by placing it under vacuum at greater than $10^{-4}$ Torr and passing sufficient voltage across it until it glows for a few seconds. After outgassing of the source, the voltage is turned to zero and the vacuum slowly released from the system.

The source is subsequently loaded with a weighed charge of 99.999+% pure gold wire which had been wrapped into a ball of sufficient size to be held within the W wire basket and is then put into place in the system.

A weighed Teflon membrane substrate is then placed at least 10 inches either above or below the source onto the target plate. Pains are taken to make sure that the membrane lays flat and does not move from the target plate.

The system is closed by placing a bell jar in position and a vacuum greater than $10^{-4}$ Torr is applied to the system.

Upon application of the vacuum, voltage is applied slowly across the source until gold can be seen to melt and wet the W wire basket. As this is occurring the gold charge will be outgassing also.

The voltage is then slowly increased until gold can be seen condensing onto the Teflon substrate. (The rate must be controlled such that the gold melt within the W wire basket does not fall out in globules or all at once). Once the gold charge has been depleted the voltage is turned to zero and the vacuum is slowly released. After the vacuum has been released the substrate+gold deposit are weighed and if the gold loading is less than 2.5 mg/cm$^2$ the vacuum deposition steps are repeated until the desired loading is obtained.

EXAMPLE II

An electrochemical sensor as described above containing an anode and cathode each comprised of a Teflon membrane (Zitex) having vapor deposited therein a layer of 2500 Å pure gold, and a Pt/air reference electrode was used for the detection of H$_2$S. The anode was operated under potentiostatic control at 1.4 V vs RHE in 18% HCLO$_4$ aqueous electrolyte. Comparative performance for H$_2$S detection in the presence of CO is shown in Table I. Gas mixtures of H$_2$S/N and CO/Air were analyzed sequentially in the electrochemical cell.

TABLE I

PERFORMANCE OF H$_2$S DETECTION SYSTEM

| GAS MIXTURE | CURRENT (uA) | SENSITIVITY (uA/ppm) | SELECTIVITY RATIO | PPM INTERFERENT/ PPM/H$_2$O |
|---|---|---|---|---|
| 27 ppm H$_2$S/N$_2$ | 12.5 | 0.46 | 1.0 | |
| 9920 ppm CO/Air | <.05 | <5 × 10$^{-6}$ | >90,000 | |

The results reported in Table I demonstrate the high selectivity of the electrochemical sensor of the invention for H$_2$S in the presence of CO.

EXAMPLE III

An electrochemical sensor as described above containing an anode and cathode each comprised of a Teflon membrane (Zitex) having vapor deposited thereon as a film (approx. 2,500 Å thick) 0.3 mg/cm$^2$ of pure gold, and a Pt/air reference electrode was used to detect H$_2$S. The electrode was potentiostatically controlled at 0.1 V vs. the Pt/Air reference electrode in a 23% KOH aqueous electrolyte. Selectivity performance characteristics for this cell are given in Table II and gas mixtures were introduced into the analyzer system sequentially. With the marked improvement of H$_2$S/NO$_2$ signal ratios over the prior art (a 2:1 signal ratio is observed in U.S. Pat. No. 4,127,462) of three orders of magnitude, accurate and non-interfering analysis of H$_2$S in gases and vapors is possible in the presence of substantial concentrations of NO$_2$. The results are summarized in Table II.

TABLE II

PERFORMANCE CHARACTERISTICS OF H$_2$S ANALYZING SYSTEM

| GAS MIXTURE | SENSITIVITY uA/ppm | PPM INTERFERENT/PPM |
|---|---|---|
| 23 PPM H$_2$S/N$_2$ | 20.9 | 1.0 |
| 585 PPM CO/Air | 0.0006 | 34830 |
| 3.3 PPM NO$_2$/Air | 0.009 | 2322 |
| 24.6 PPM NO/Air | 0.002 | 10450 |
| 50 PPM NH$_3$/Air | 0.054 | 387 |

It is claimed:

1. An electrochemical sensing device comprising a sensing electrode, a counterelectrode, an electrolyte in contact with said sensing electrode and counterelectrode, said sensing electrode comprising a porous hydrophobic polytetrafluoroethylene substrate having vapor deposited or sputtered thereon a porous gold film catalyst whose thickness is in the range of 200 Å to 20,000 Å to provide a diffusion electrode, said film of gold being subjected to reduction in the presence of H$_2$ to enhance its stability and ability to selectively detect gases, means for exposing said sensing electrode to the gas to be detected, means electrically coupled to said sensing electrode for maintaining said sensing electrode at a potential of about 0.4 volts to about 1.5 volts with respect to the potential of the reversible hydrogen couple in the electrolyte of said cell, and means for measuring current flowing between said sensing electrode and said counterelectrode which measured current is a measure of the concentration of the noxious gas being detected.

2. An electrochemical sensing device comprising a sensing electrode, a counterelectrode, an electrolyte in contact with said sensing electrode and counterelectrode, said sensing electrode comprising a porous hydrophobic polytetrafluoroethylene substrate having vapor deposited or sputtered thereon a porous gold film catalyst whose thickness is in the range of 200 Å to 20,000 Å to provide a diffusion electrode, said film of gold being subjected to oxidation in the presence of O$_2$ to enhance its stability and ability to selectively detect gases, means for exposing said sensing electrode to the gas to be detected, means electrically coupled to said sensing electrode for maintaining said sensing electrode at a potential of about 0.4 volts to about 1.5 volts with respect to the potential of the reversible hydrogen couple in the electrolyte of said cell, and means for measuring current flowing between said sensing electrode and said counterelectrode which measured current is a measure of the concentration of the noxious gas being detected.

3. A method for electrochemically detecting a noxious gas in the presence of carbon monoxide which comprises feeding a gaseous sample containing said gas to the sensing electrode of an electrochemical cell comprising a sensing electrode, a counterelectrode, an electrolyte in contact with said sensing electrode and counterelectrode, said sensing electrode comprising a porous polytetrafluoroethylene substrate having vapor-deposited thereon a porous film of gold ranging in thickness between 200 Å and 20,000 Å to provide a diffusion electrode, reducing said film of gold in the presence of hydrogen to enhance its stability and ability to selectively detect gases, maintaining the sensing electrode at a potential of about 0.4 volts to about 1.5 volts with respect to the potential of the reversible hydrogen couple in the electrolyte of said cell, and measuring current flowing between said sensing electrode and said counterelectrode which measured current is a measure of the concentration of the noxious gas being detected.

4. A method for electrochemically detecting a noxious gas in the presence of carbon monoxide which comprises feeding a gaseous sample containing said gas to the sensing electrode of an electrochemical cell comprising a sensing electrode, a counterelectrode, an electrolyte in contact with said sensing electrode and counterelectrode, said sensing electrode comprising a porous polytetrafluoroethylene substrate having vapor-deposited thereon a porous film of gold ranging in thickness between 200 Å and 20,000 Å to provide a diffusion electrode, oxidizing said film of gold in the presence of $O_2$ to enhance its stability and ability to selectively detect gases, maintaining the sensing electrode at a potential of about 0.4 volts to about 1.5 volts with respect to the potential of the reversible hydrogen couple in the electrolyte of said cell, and measuring current flowing between said sensing electrode and said counterelectrode which measured current is a measure of the concentration of the noxious gas being detected.

5. A method according to claim 4 wherein the thickness of the film is between 2,000 Å and 10,000 Å.

* * * * *